United States Patent
Geva et al.

(10) Patent No.: US 10,251,603 B2
(45) Date of Patent: Apr. 9, 2019

(54) SYSTEMS AND METHODS FOR VITAL SIGNS MONITORING WITH EAR PIECE

(71) Applicants: Nir Geva, Ness Ziona (IL); Yacov Geva, London (GB)

(72) Inventors: Nir Geva, Ness Ziona (IL); Yacov Geva, London (GB)

(73) Assignee: G-MEDICAL INNOVATIONS HOLDINGS LTD. (KY)

( * ) Notice: Subject to any disclaimer, the term of this patent is extended or adjusted under 35 U.S.C. 154(b) by 6 days.

(21) Appl. No.: 15/026,258

(22) PCT Filed: Jan. 26, 2016

(86) PCT No.: PCT/IL2016/050084
§ 371 (c)(1),
(2) Date: Mar. 31, 2016

(87) PCT Pub. No.: WO2016/120870
PCT Pub. Date: Aug. 4, 2016

(65) Prior Publication Data
US 2017/0079586 A1    Mar. 23, 2017

Related U.S. Application Data

(60) Provisional application No. 62/107,528, filed on Jan. 26, 2015.

(51) Int. Cl.
*A61B 5/00* (2006.01)
*A61B 5/0408* (2006.01)
(Continued)

(52) U.S. Cl.
CPC .......... *A61B 5/6815* (2013.01); *A61B 5/0006* (2013.01); *A61B 5/0008* (2013.01);
(Continued)

(58) Field of Classification Search
CPC ....... A61B 5/00; A61B 5/0059; A61B 5/0205; A61B 5/021; A61B 5/11; A61B 5/14546;
(Continued)

(56) References Cited

U.S. PATENT DOCUMENTS

2005/0101872 A1    5/2005  Sattler et al.
2006/0084878 A1*   4/2006  Banet ................... A61B 5/0205
                                                          600/485
(Continued)

*Primary Examiner* — Carl H Layno
*Assistant Examiner* — Jon Eric C Morales
(74) *Attorney, Agent, or Firm* — Reches Patents

(57) ABSTRACT

A vital signs monitoring system, the system including: (a) an ear device including: a curved body adapted to a shape of an ear, an upper end, a lower end, two opposite facing sides, a first side adapted to be proximal a skull and a second side adapted to be proximal an earlobe, the ear device including: (i) a temperature sensor adapted to sense a body temperature from a depression between a lower jawbone and skull; and (b) a control system, including a processor and a memory, configured and operable to control operation of the ear device, to collect signals received from at least one sensor including the temperature sensor, to process the signals to provide medically significant results.

23 Claims, 11 Drawing Sheets

(51) Int. Cl.
  *A61B 5/024* (2006.01)
  *A61B 5/0205* (2006.01)
  *A61N 1/04* (2006.01)
  *A61N 1/36* (2006.01)
  *A61N 1/372* (2006.01)
  *A61B 5/0404* (2006.01)
  *A61B 5/20* (2006.01)
  *A61B 5/021* (2006.01)
  *A61B 5/0402* (2006.01)
  *A61B 5/1455* (2006.01)

(52) U.S. Cl.
  CPC .......... *A61B 5/0024* (2013.01); *A61B 5/0086* (2013.01); *A61B 5/024* (2013.01); *A61B 5/02055* (2013.01); *A61B 5/0404* (2013.01); *A61B 5/04085* (2013.01); *A61B 5/04087* (2013.01); *A61B 5/20* (2013.01); *A61B 5/4836* (2013.01); *A61B 5/4848* (2013.01); *A61N 1/0456* (2013.01); *A61N 1/0484* (2013.01); *A61N 1/36021* (2013.01); *A61N 1/36025* (2013.01); *A61N 1/37252* (2013.01); *A61B 5/021* (2013.01); *A61B 5/02416* (2013.01); *A61B 5/02438* (2013.01); *A61B 5/0402* (2013.01); *A61B 5/14551* (2013.01); *A61B 5/14552* (2013.01); *A61B 5/6816* (2013.01); *A61B 2562/222* (2013.01)

(58) Field of Classification Search
  CPC ......... A61B 5/411; A61B 5/415; A61B 5/418; A61B 5/6817; A61B 5/6887; A61B 5/1112; A61B 5/1032; A61B 5/4812; A61B 5/14556; A61B 5/14539; A61B 5/4866
  USPC .................................................. 600/300, 301
  See application file for complete search history.

(56) References Cited

U.S. PATENT DOCUMENTS

| | | |
|---|---|---|
| 2007/0250145 A1 | 10/2007 | Kraus et al. |
| 2008/0146890 A1* | 6/2008 | LeBoeuf .............. A61B 5/0059 600/300 |
| 2008/0200774 A1* | 8/2008 | Luo ...................... A61B 5/0002 600/301 |
| 2011/0286615 A1 | 11/2011 | Olodort |
| 2014/0275888 A1 | 9/2014 | Wegerich et al. |

* cited by examiner

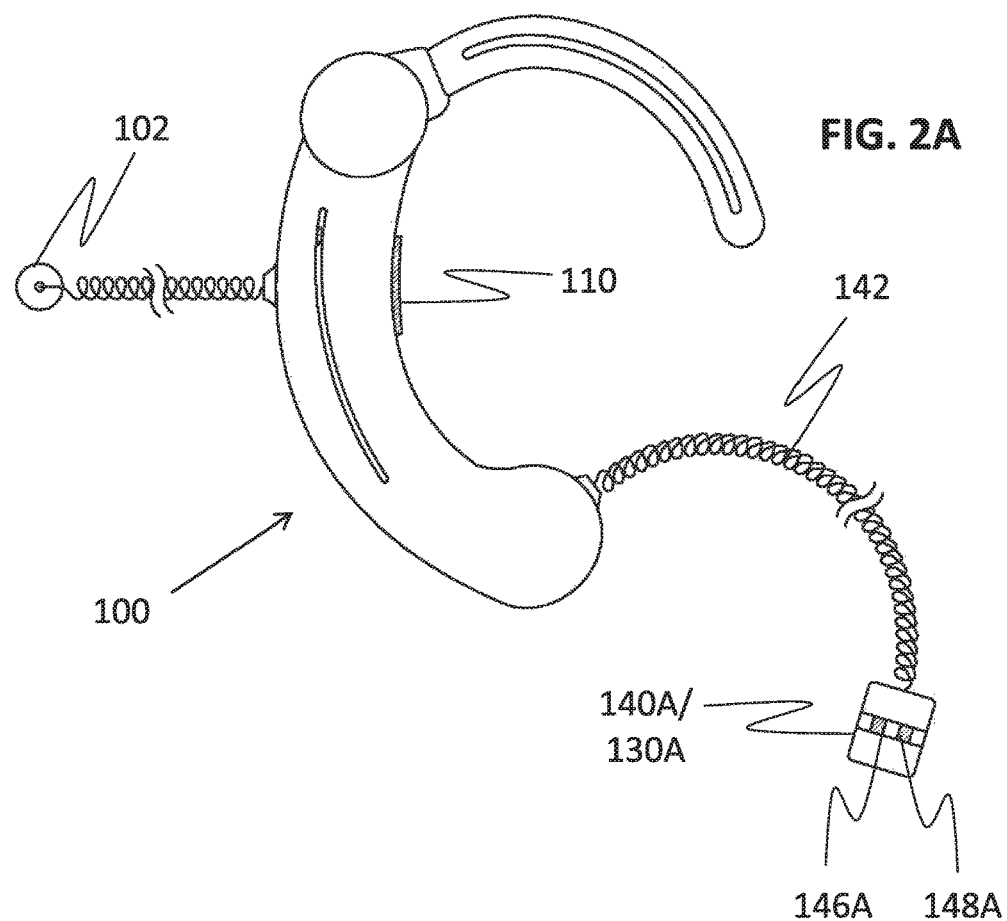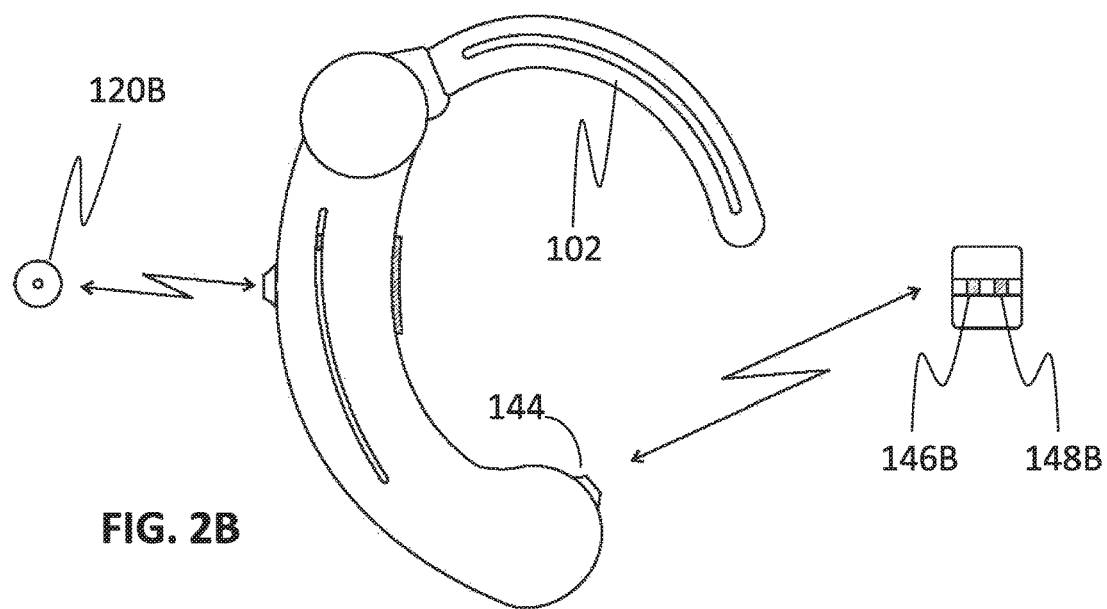

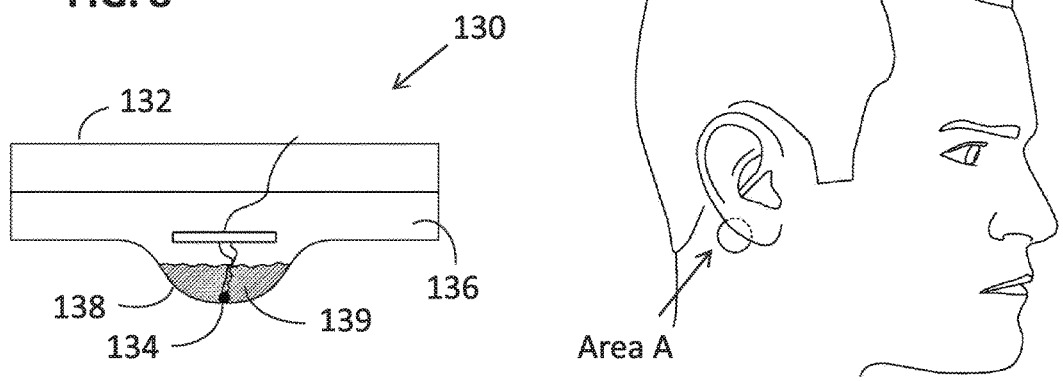
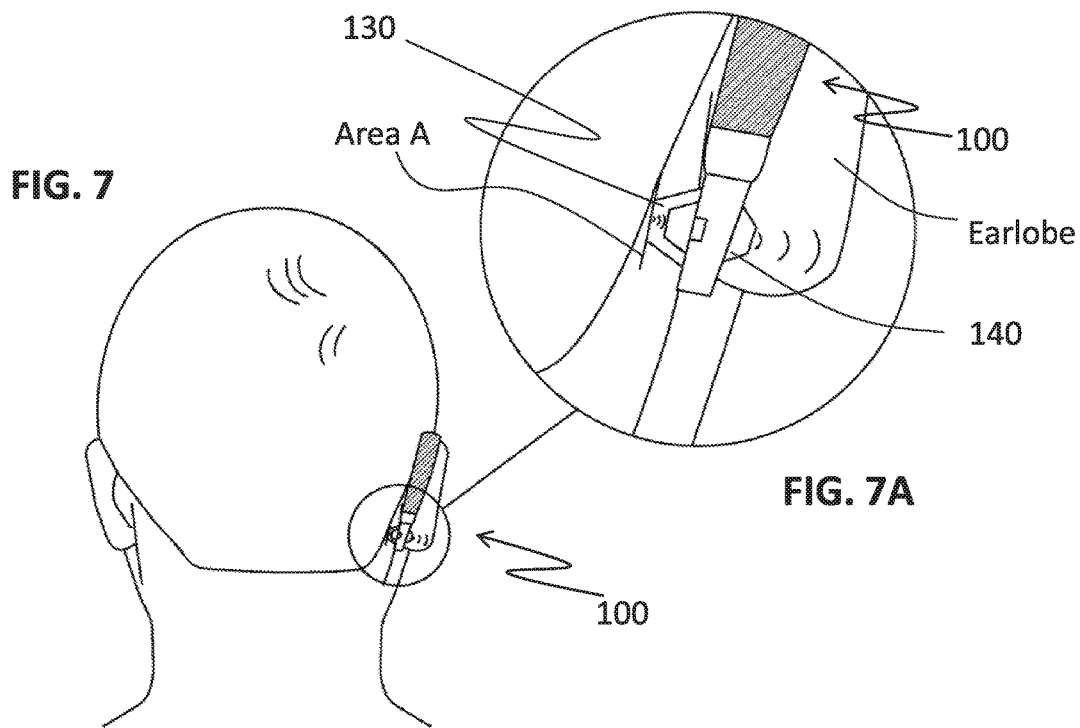

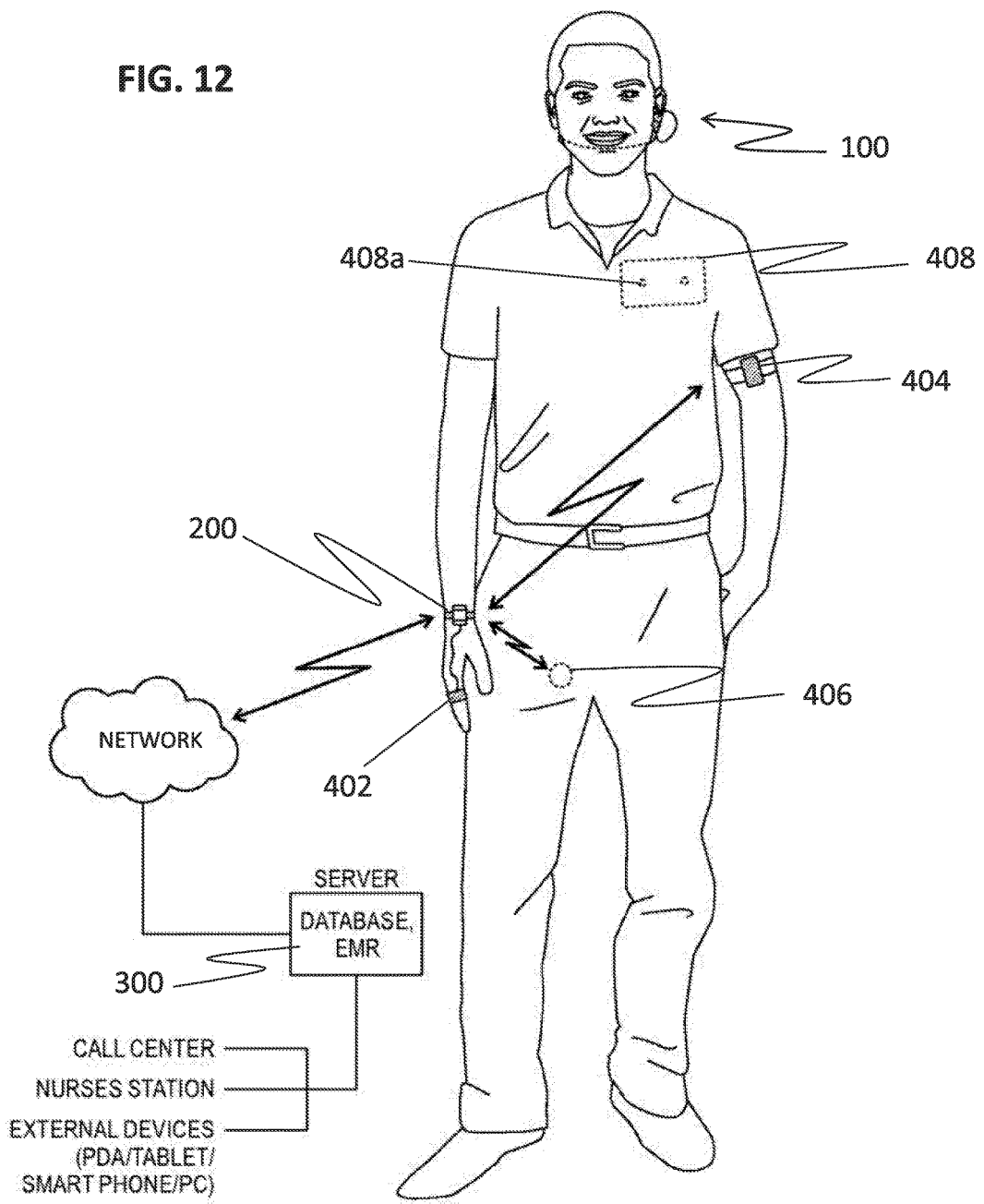

SYSTEMS AND METHODS FOR VITAL SIGNS MONITORING WITH EAR PIECE

This patent application claims priority from and the benefit of PCT/IL2016/050084 which claims benefit of U.S. Provisional Patent Application No. 62/107,528, filed Jan. 26, 2015, which is incorporated in its entirety as if fully set forth herein.

FIELD OF THE INVENTION

The present invention relates to a device, system and methods for monitoring vital signs and, more particularly, to an ear-worn device that gathers sensor data via integrated sensors and/or remotely located sensors on the same body.

BACKGROUND OF THE INVENTION

A relatively high proportion of the human population suffers from various long term medical conditions such as high blood pressure, cardiac arrhythmia and/or diabetes. These conditions are factors in increased risk of stroke, nevertheless many of those suffering from such conditions are not treated properly due to unawareness or difficulties in diagnosis. Moreover, large parts of the population live with symptoms which may be indicative of increased likelihood of health conditions such as cardiac ischemia that may lead to Myocardial Infarction (Heart Attack) and other harmful events.

The monitoring of physiological parameters may provide insight to symptoms and can uncover conditions that may develop into adverse health conditions. The description above is presented as a general overview of related art in this field and should not be construed as an admission that any of the information it contains constitutes prior art against the present patent application.

SUMMARY OF THE INVENTION

According to the present invention there is provided a vital signs monitoring system, the system including: (a) an ear device including: a curved body adapted to a adapted to be proximal a skull and a second side adapted to be proximal an earlobe, the ear device including; (i) a temperature sensor adapted to sense a body temperature from a depression between a lower jawbone and skull; and (b) a control system, including a processor and a memory, configured and operable to control operation of the ear device, to collect signals received from at least one sensor including the temperature sensor, to process the signals to provide medically significant results.

According to further features in preferred embodiments of the invention described below the temperature sensor is an infra red (IR) sensor configured to measure IR radiation at the depression, the IR radiation emitted from a carotid artery.

According to still further features in the described preferred embodiments the temperature sensor includes a thermistor where the thermistor is encased in a casing, insulated, and held in place by a thermally conductive adhesive, the casing having a thermally conductive surface adapted to abut the depression.

According to still further features the ear device further includes: (ii) a first electrode built into an inner curve of the curved body, the first electrode configured to sense signal from behind the ear; and (iii) a second electrode distanced from, and in electric communication with, the ear device, wherein the first and the second electrodes are adapted to be positioned so as to create a vector required for acquiring electrocardiographic measurements, wherein the second electrode is operationally coupled to the ear device via one of: a cable and a wireless communications component.

According to still further features the ear device further includes: (ii) a blood oxygen sensor configured to receive signals that are processed to receive the medically significant results selected from the group including: a photoplethysmogram (PPG), a peripheral oxygen saturation (SpO2) measurement, a heart rate, a combination of at least two the results, wherein the blood oxygen sensor is selected from the group including: a transmissive sensor and a reflective sensor, and wherein the blood oxygen sensor is operationally coupled to the ear device via a connection selected from the group including: a wired connection and a wireless connection.

According to still further features the ear device further includes an earlobe attachment that is adapted to abut an outer surface of an earlobe of the ear, the earlobe attachment including a photodector to receive light energy from a light source of the blood oxygen sensor during a transmissive pulse oximetry event.

According to still further features the system further includes (c) at least one additional sensor adapted to be in electrical communication with a body part so as to receive electrical signals from the body part, wherein the at least one additional sensor is in electrical communication with the ear device, the electrical communication effected by at least one of a wireless connection and a wired connection.

According to still further features the at least one additional sensor is an auxiliary ear device, wherein the auxiliary ear device has a curved body adapted to a shape of an ear and adapted to be worn a second ear on a facing side of a head, distanced from the ear device.

According to still further features the at least one additional sensor is selected from the group including: blood oxygen sensor, a heart rate sensor, a blood pressure sensor, a urine sensor, a urine level sensor, a medication level sensor, a medication inducing sensor and a combination sensor including at least two of the sensors.

According to still further features the system further includes (c) at least one electrode operationally coupled to the ear device, the at least one electrode configured to deliver electrical pulses from a power source in the ear device to a skin patch operationally coupled to the at least one electrode.

According to still further features the system further includes (c) a gateway device including: a short-distance communication module for communicating with the ear device, a processor, memory, and a long-distance communication module for communicating with an external back-end computer, wherein the gateway device is embodied in a device selected from the group including: a handheld device, a portable computing device and a body worn device.

According to still further features the system further includes (d) at least one additional sensor adapted to be in electrical communication with a body part so as to receive electrical signals from the body part, wherein the at least one additional sensor in electrical communication with at least one of the ear device and the gateway device, the electrical communication effected by at least one of a wireless connection and a wired connection.

According to still further features the ear device further includes: an anchor member operationally coupled to the upper end of the ear device and adapted to support the ear device on the ear, the anchor member having a speaker embedded therein and a microphone embedded in the lower end of the ear device.

According to still further features the microphone is a wire microphone that extends out of the lower end of the ear device by manually manipulating a slider along a channel, the slider and channel integrated in the ear device.

According to another embodiment there is provided a vital signs monitoring system, the system including: (a) an primary ear device including: a curved body adapted to a shape of an ear, an upper end, a lower end, two opposite facing sides, a first side adapted to be proximal a skull and a second side adapted to be proximal an earlobe, the ear device including at least one sensor; (b) a secondary ear device adapted to be worn a second ear on a facing side of a head, distanced from the primary ear device, the secondary ear device in electrical communication with the primary ear device, the electrical communication effected by at least one of a wireless connection and a wired connection; and (c) a control system embedded in the primary device including a processor and a memory, configured and operable to control operation of the primary and secondary ear devices, to collect signals received from at least one sensor, to process the signals to provide medically significant results.

According to another embodiment there is provided a vital signs monitoring system, the system including: (a) an ear device including: a curved body adapted to a shape of an ear, an upper end, a lower end, two opposite facing sides, a first side adapted to be proximal a skull and a second side adapted to be proximal an earlobe, the ear device including at least one vital signs sensor; and (b) at least one electrode operationally coupled to the ear device, the at least one electrode configured to deliver electrical pulses from a power source in the ear device to a skin patch operationally coupled to the at least one electrode. (c) a control system, including a processor and a memory, configured and operable to control operation of the ear device, to collect signals received from the at least one vital signs sensor, to process the signals to provide medically significant results and to control delivery of the electrical pulses.

According to another embodiment there is provided a vital signs monitoring system, the system including (a) an ear device including: a curved body adapted to a shape of an ear, an upper end, a lower end, two opposite facing sides, a first side adapted to be proximal a skull and a second side adapted to be proximal an earlobe, the ear device including at least one vital signs sensor; and (b) a control system, including a processor and a memory, configured and operable to control operation of the ear device, to collect signals received from the at least one vital signs sensor, to process the signals to provide medically significant results.

According to further features the system further includes: (c) a chest device operationally coupled to a biocompatible adhesive patch adapted to be adhered to skin, the chest device including at least some of: amplifiers, filters, analog-to-digital converters, a local memory and a local processor with a short range wireless communications component, wherein the chest device is configured to acquire electrical signals via the biocompatible adhesive patch, filter and digitize the signals and send the digitized signals to the ear device to process the signals to provide the medically significant results.

BRIEF DESCRIPTION OF THE DRAWINGS

Various embodiments are herein described, by way of example only, with reference to the accompanying drawings, wherein:

FIGS. 2A and 2B are diagrams that illustrate two additional embodiments of the ear device of the immediate system;

FIG. 6 is a perspective view of the client head with than area A indicated behind the ear;

FIGS. 7 and 7A are diagrams of view of a client head with an exemplary embodiment of the ear device in position behind the right ear;

FIG. 8 is a diagram of an exemplary embodiment of the thermometer of the system;

FIG. 12 is a diagram illustrating an example of the immediate system;

DESCRIPTION OF THE PREFERRED EMBODIMENTS

Figure 1A:
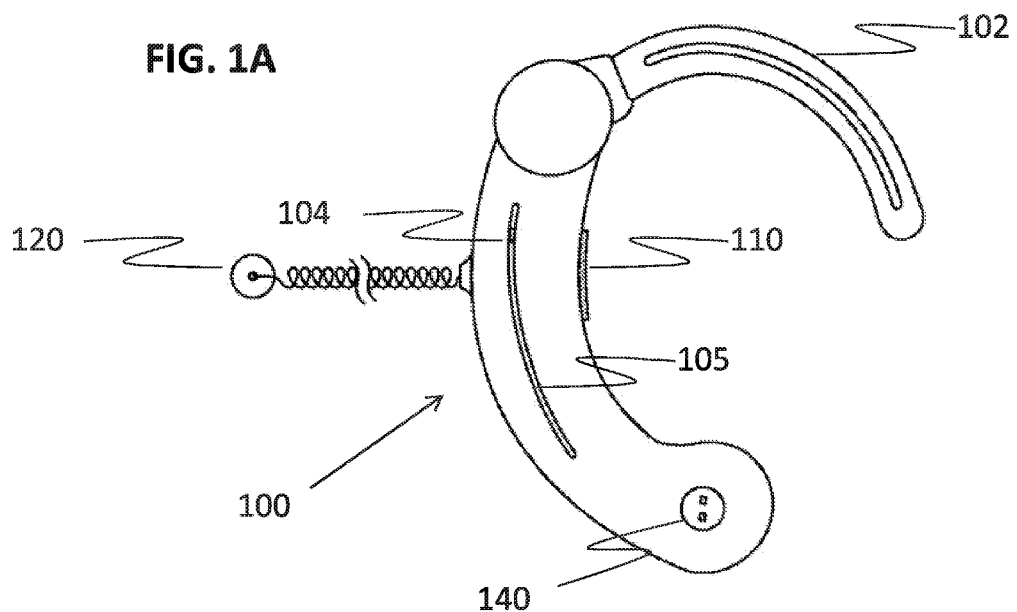
FIGS. 1A and 1B are diagrams illustrating front and back views respectively of an exemplary main unit of a system for monitoring of vital signs.

In order to understand the invention and to see how it may be carried out in practice, embodiments will now be described, by way of non-limiting example only, with reference to the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In the drawings and descriptions set forth, identical reference numerals indicate those components that are common to different embodiments or configurations.

Unless specifically stated otherwise, as apparent from the following discussions, it is appreciated that throughout the specification discussions utilizing terms such as "processing", "calculating", "computing", "determining", "generating", "setting", "configuring", "selecting", "defining", or the like, include action and/or processes of a computer that manipulate and/or transform data into other data, the data represented as physical quantities, e.g. such as electronic quantities, and/or the data representing the physical objects. The terms "computer", "processor", and "controller" should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and or any combination thereof.

The operations in accordance with the teachings herein may be performed by a computer specially constructed for the desired purposes or by a general purpose computer specially configured for the desired purpose by a computer program stored in a computer readable storage medium.

As used herein, the phrase "for example," "such as", "for instance" and variants thereof describe non-limiting embodiments of the presently disclosed subject matter. Reference in the specification to "one case", "some cases", "other cases" or variants thereof means that a particular feature, structure or characteristic described in connection with the embodiment(s) is included in at least one embodiment of the presently disclosed subject matter. Thus the appearance of the phrase "one case", "some cases", "other cases" or variants thereof does not necessarily refer to the same embodiment(s).

The methods and/or processes disclosed herein may be implemented as a computer program product such as, for example, a computer program tangibly embodied in an information carrier, for example, in a non-transitory computer-readable or non-transitory machine-readable storage device and/or in a propagated signal, for execution by or to control the operation of, a data processing apparatus including, for example, one or more programmable processors and/or one or more computers. The terms "non-transitory computer-readable storage device" and "non-transitory machine-readable storage device" encompasses distribution media, intermediate storage media, execution memory of a computer, and any other medium or device capable of storing for later reading by a computer program implementing embodiments of a method disclosed herein. A computer program product can be deployed to be executed on one computer or on multiple computers at one site or distributed across multiple sites and interconnected by a communication network.

In the discussion, unless otherwise stated, adjectives such as "substantially" and "about" that modify a condition or relationship characteristic of a feature or features of an embodiment of the invention, are to be understood to mean that the condition or characteristic is defined to within tolerances that are acceptable for operation of the embodiment for an application for which it is intended.

Positional terms such as "upper", "lower" "right", "left", "bottom", "below", "lowered", "low", "top", "above", "elevated", "high", "vertical" and "horizontal" as well as grammatical variations thereof as may be used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed in a diagonal orientation or position, placed horizontally or vertically, or similarly modified. Accordingly, it will be appreciated that the terms "bottom", "below", "top" and "above" may be used herein for exemplary purposes only, to illustrate the relative positioning or placement of certain components, to indicate a first and a second component or to do both. "Coupled with" means indirectly or directly "coupled with".

The term "proximal" refers to a location close to a main body mass and the term "distal" refers to a location which is relatively distanced from the main body mass.

Where applicable, although state diagrams, flow diagrams or both may be used to describe embodiments, the technique is not limited to those diagrams or to the corresponding descriptions. For example, flow need not move through each illustrated box or state, or in exactly the same order as illustrated and described.

It is appreciated that certain features of the presently disclosed subject matter, which are, for clarity, described in the context of separate embodiments, may also be provided in combination in a single embodiment. Conversely, various features of the presently disclosed subject matter, which are, for brevity, described in the context of a single embodiment, may also be provided separately or in any suitable subcombination.

In embodiments of the presently disclosed subject matter one or more stages illustrated in the figures may be executed in a different order and/or one or more groups of stages may be executed simultaneously and vice versa. The figures illustrate a general schematic of the system architecture in accordance with an embodiment of the presently disclosed subject matter. Each module in the figures can be made up of any combination of software, hardware and/or firmware that performs the functions as defined and explained herein. The modules in the figures may be centralized in one location or dispersed over more than one location.

Figure 1B:
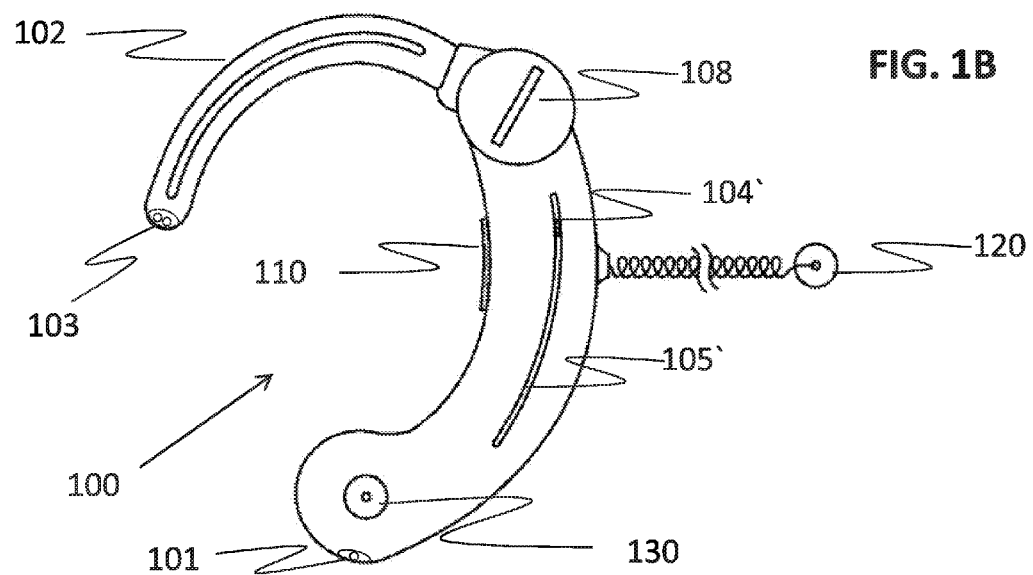

FIGS. 1A and 1B are diagrams illustrating front and back views respectively of an exemplary main unit 100 of a system for monitoring of vital signs, in accordance with the presently disclosed subject matter. The system includes a casing 100 which includes various electronic components, few examples of which are discussed below. The ear device has a curved body that is adapted to the shape of a human ear, an upper end, a lower end, two opposite facing sides, a first side adapted to be proximal a skull and a second side adapted to be proximal an earlobe. The unit includes a shaped anchor 102 for holding the unit near to an ear of a wearer of the system (also referred to as the "client"), without the client having to hold it. The shaped anchor may be part of the casing (e.g. as exemplified in FIGS. 1A and 1B), or otherwise be connected to it. The shape of the shaped anchor may be similar to that use in hearing aids, which connect the hearing aid to the ear of the client for use in most daily activities without falling off. In one embodiment, the anchor is retractable with a slider 104 along a channel 105 which extends and retracts the anchor piece for the user to select a comfortable anchor length.

The system (and especially the main unit) may optionally include one or more internal power sources (a battery, primary or secondary). In one embodiment, the power source is a rechargeable battery which may be recharged via a physical power interface (e.g. a power socket). In another embodiment, the battery may be a replaceable battery that can be removed and changed by a user or a technician. Exemplarily, a compartment 108 (see FIGS. 1B and 3B) houses a button battery that can be accessed and replaced using a flat-tipped screwdriver, as known in the art.

Optionally, the system (e.g. as part of the main unit) may include a microphone and/or a speaker. Exemplarily, a speaker 103 is integrated into the distal end of the anchor piece 102 and the microphone 101 is integrated into the sensor end of the primary unit casing. In another embodiment, the microphone is a wire microphone that extends out of the lower, sensor end of the casing by manually manipulating a second slider 104' which moves along a second channel 105'.

Such microphone, if implemented, can sense ambient sounds, and the processor in such a case may use such sound information for correlating physiological data (determined by the vital signs) and environment data (e.g. in monitoring sleep tests).

The speaker, if implemented, may be used, for example, to enable vocal communication with the client in case needed (e.g. the client may be addressed by a central monitoring center in which the back-end unit is located). The main unit in such case may operate similarly to a Bluetooth headset, where a gateway (see FIGS. 11-15) will operate as the cellular telephony communication unit mediating between the remote caller and the headset component (the main unit).

Optionally, the system (e.g. as part of the main unit or the gateway) may include a global positioning system (GPS) unit, enabling to locate the client if lost. For example, when the system is near a BLE/BT/Zigbee open network connection, the location of the system (and thus of the client) can be transmitted via a cellular and/or WiFi communication channel connected to the RF channel.

In preferred embodiments, the system includes an electrocardiography (ECG) device (the processor of which may be included within the casing, and is therefore not illustrated in FIGS. 1A-1B), which includes at least two electrodes. One or more of the electrodes are preferably embedded in the casing, and wearable next to the ear. Exemplarily, a first electrode 110 is built into the inner curve of the ear piece 100 which sits against the skin of the client, behind the ear. One or more of the electrodes may be distanced from the casing and connected thereto using a cable. Exemplarily a second electrode 120 is coupled via a cable 122 the outer rim of the ear device 100.

The system may further include additional sensors. For example, the system may include a temperature sensor 130, for measuring a temperature of the client. the temperature sensor may be embedded into the casing wearable next to the ear, and/or it may be distanced from the casing and connected thereto using a cable or a wireless connection. In the exemplary embodiment shown in FIGS. 1A-B, the temperature sensor is used to measure temperature behind the ear. The sensor 130 is embedded in the back side of the unit which is shown in FIG. 1B. The back side of the unit is the proximal side of the unit which is next to the skull. The front side of the unit is the distal side of the unit which is next to the back surface of the ear. In other embodiments, the sensor is used to measure temperature inside the ear. In such cases the sensor is located in an auxiliary unit which is external to the casing of the ear device and which may be inserted into an ear of the client, optionally connected to the casing using a cable (see FIG. 4). In still further embodiments the temperature is measured at other locations. For example, temperature can be measured at a different location on the head of the client (see FIG. 10), or next to another external unit wired or wirelessly connected to a communication module built into the casing (see FIG. 5).

In preferred embodiments, the system includes an oxygen sensor 140 (for measuring oxygen levels and/or oxygen saturation level, PPG/SPO2). In the exemplary embodiment shown in FIGS. 1A-B, the oxygen sensor is embedded into the casing wearable next to the ear. In other embodiments, the oxygen sensor may be distanced from the casing and connected thereto using a cable or a wireless connection (e.g. see FIGS. 2A and 2B respectively). The oxygen sensor may be used to measure oxygen levels when located behind the ear (e.g. if embedded in the casing), inside the ear (e.g. if located in an auxiliary unit which is external to the casing and which may be inserted into an ear of the client, optionally connected to the casing using a cable), fitted to the earlobe (e.g. if the ear device includes an earlobe attachment), or in other locations (e.g. other location on the head of the client, or next to another external unit wirelessly connected to a communication module built into the casing).

Figure 4:
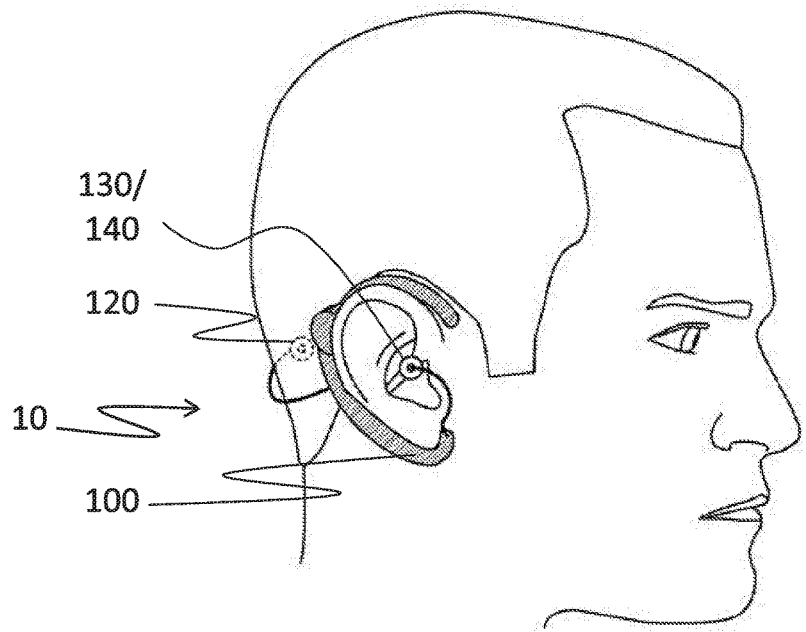
FIG. 4 is a diagram illustrating a system of the immediate invention as worn on a person.

FIGS. 2A and 2B are diagrams that illustrate two additional embodiments of the ear device of the immediate system. In FIG. 2A the oxygen sensor 140A is located in an auxiliary unit which is external to the casing. The auxiliary unit is connected to the casing using a cable 142. The auxiliary unit may be inserted in an ear of the client, as depicted in FIG. 4. Alternatively, the auxiliary unit may be adhered to another part of the body or head, e.g., as depicted in Fig. A. In FIG. 2B the oxygen sensor 140B is located in an auxiliary unit which is external to the casing. The auxiliary unit is wirelessly connected to the casing by a wireless transceiver 144. Wireless communication is discussed elsewhere in further detail.

Figure 3A:
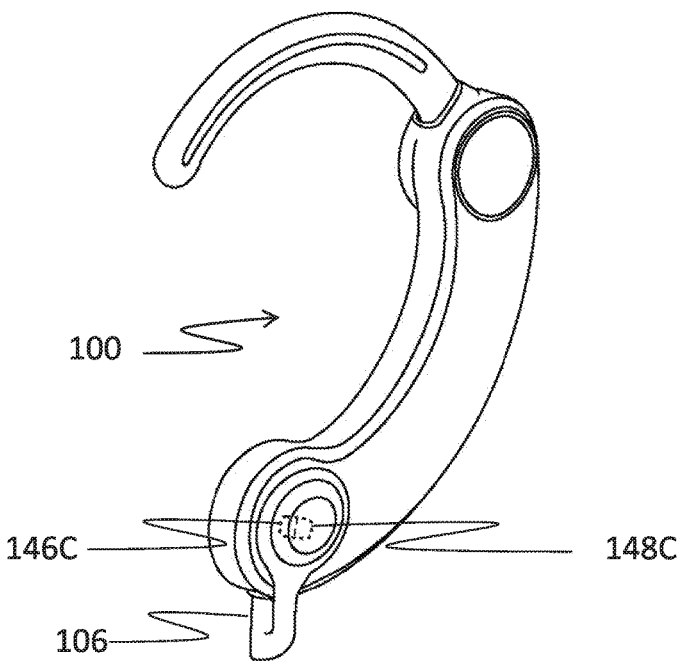
FIGS. 3A and 3B are diagrams that illustrate front and back views respectively of another exemplary embodiment of the ear device of the system.
Figure 3B:
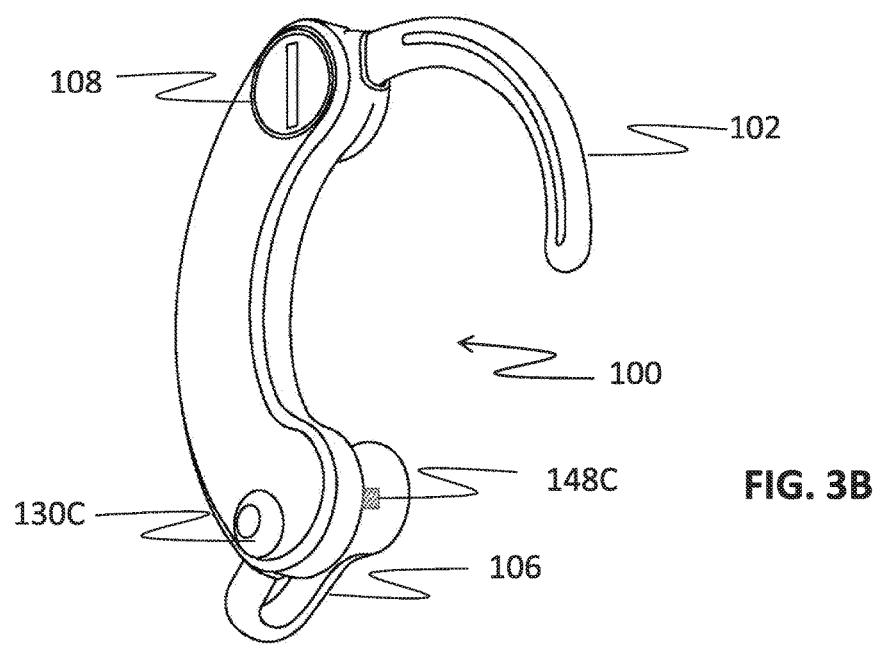

FIGS. 3A and 3B are diagrams that illustrate front and back views respectively of another exemplary embodiment of the ear device 100 of the system for monitoring of vital signs, in accordance with the presently disclosed subject matter. The immediate embodiment of the main unit is similar to the embodiment of the main unit shown in FIGS. 1A and 1B with the addition of an earlobe attachment 106. The earlobe attachment includes various components that are used to help measure heart rate, blood pressure, and other vital signs. On the back side of the ear device 100, which is depicted in FIG. 3B, a thermometer 130C is located at the bottom section of the device, on the opposite side of the device to the earlobe attachment.

Specifically, the earlobe attachment 106 is preferably used for transmissive pulse oximetary. Peripheral capillary oxygen saturation (SpO2) is an estimation of the oxygen saturation level usually measured with a pulse oximeter device. The saturation level can be calculated with the pulse oximetry.

Pulse oximetry is a noninvasive method for monitoring a person's oxygen saturation (SO2). A pulse oximetry reading of SpO2 (peripheral oxygen saturation) is not always identical to the reading of SaO2 (arterial oxygen saturation) from arterial blood gas analysis, but the two are reliably enough correlated that the safe, convenient, noninvasive, inexpensive pulse oximetry method is valuable for measuring oxygen saturation in clinical use.

The transmissive application mode is the most common mode of pulse oximetry. In the transmissive mode, a sensor device is placed on a thin part of the patient body, usually a fingertip or earlobe, or in the case of an infant, across a foot. The device passes two wavelengths of light through the body part to a photodetector. The device measures the changing absorbance at each of the wavelengths, allowing the device to determine the light absorbance due to the pulsing arterial blood alone, excluding venous blood, skin, bone, muscle, fat, and (in most cases) nail polish.

In the immediate embodiment shown in FIGS. 3A-B, an oxygen sensor 140C includes a light source 146 and a photodetector 148 (drawn in broken lines as they are obscured by the earlobe attachment). Exemplarily, the light source 146 is embedded in the lower part of the main unit casing, opposite the earlobe attachment, and the photodetector is embedded in the inner side of the earlobe attachment 106, which abuts the earlobe of the client. The light source sends two wavelengths of light through the earlobe to the photodetector. The device measures the changing absorbance at each of the wavelengths, allowing the device to determine the absorbances of the light due to the pulsing arterial blood, as discussed above. As mentioned, various other vital signs can be measured in a similar fashion.

The oxygen sensors illustrated in FIGS. 1 and 2 use reflectance pulse oximetry to measure, at least, SpO2. Reflectance pulse oximetry does not require a thin section of the client body, per se, and is therefore well suited to more universal application such as the feet, forehead and chest. That being said, the reflectance method can be very accurate when used on the earlobe.

A photoplethysmogram (PPG) is an optically obtained plethysmogram, a volumetric measurement of an organ. A PPG is often obtained by using a pulse oximeter which illuminates the skin and measures changes in light absorption. A conventional pulse oximeter monitors the perfusion of blood to the dermis and subcutaneous tissue of the skin. In preferred embodiments, the oxygen sensors 140, 140A, 140B, 140C can alternatively or additionally be pulse oximeter capable of obtaining a PPG.

With each cardiac cycle the heart pumps blood to the periphery. Even though this pressure pulse is somewhat damped by the time it reaches the skin, it is enough to distend the arteries and arterioles in the subcutaneous tissue. If the pulse oximeter is attached without compressing the skin, a pressure pulse can also be seen from the venous plexus, as a small secondary peak.

The change in volume caused by the pressure pulse is detected by illuminating the skin with the light from a light-emitting diode (LED) and then measuring the amount of light either transmitted (e.g. with earlobe attachment 106) or reflected (e.g. in embodiments without the earlobe attachment 106) to a photodiode/photodetector. Each cardiac cycle appears as a peak, as seen in the figure. Because blood flow to the skin can be modulated by multiple other physiological systems, the PPG can also be used to monitor breathing, hypovolemia, and other circulatory conditions. Additionally, the shape of the PPG waveform differs from subject to subject, and varies with the location and manner in which the pulse oximeter is attached.

Reverting back to FIGS. 1 and 2, the oxygen sensor is alternatively or additionally a pulse oximeter. Hereinafter, the sensor is referred to interchangeably as either a pulse oximeter or a PPG/SpO2 sensor. In FIG. 1A a reflective pulse oximeter 140 includes a light source 146 (e.g. an LED) and a photodetector/photodiode 148 located on the casing of the main unit.

In FIGS. 2A and 2B the reflective PPG/SpO2 sensors 140A and 140B include a light source 146A/146B and a photodetector/photodiode 148A/148B located on the same surface of the auxiliary unit. In some embodiments (not shown) the auxiliary unit may be an earlobe attachment that attaches or clips onto the other earlobe or the auxiliary unit may be a finger worn attachment. The remote auxiliary unit may be a reflective or transmissive device.

It is noted that other sensors may be used to measure other vital signs of the client, and other parameters of the client and/or of its environment. Such sensor may be, for example, a respiration sensor, a heart rate sensor, and so on.

Figure 5:
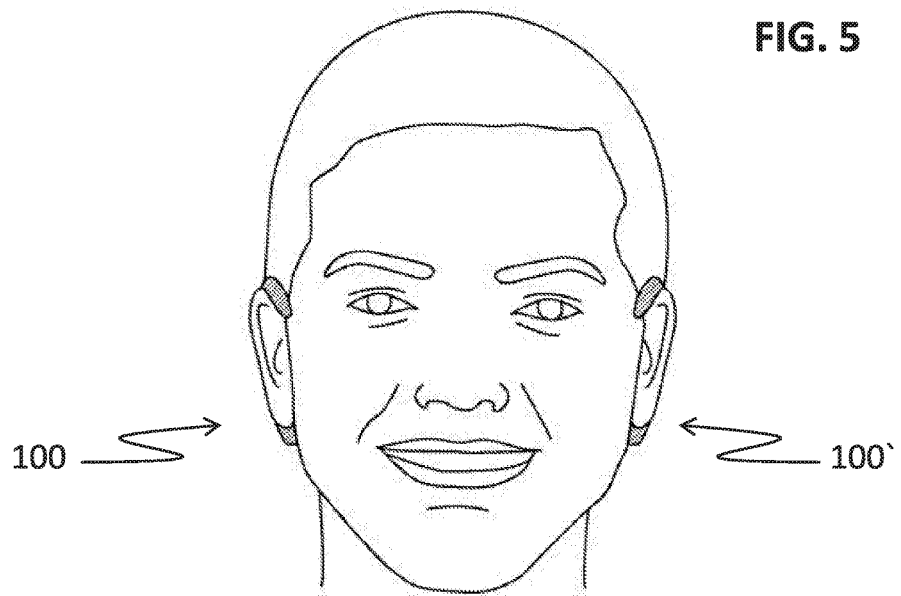
FIG. 5 is a diagram illustrating two ear-wearable units of the system.

FIGS. 4 and 5 are diagrams illustrating examples of the aforementioned system for monitoring of vital signs, in accordance with the presently disclosed subject matter, when worn by a person. FIG. 4 depicts a system 10 of the immediate invention as worn on a person. The ear device 100 is worn on the ear like a hearing aid. A first auxiliary unit is inserted in the ear of the client and a second auxiliary unit is attached to the skull at the opposite side of the head to the ear unit. Exemplarily, the first auxiliary unit, inserted in the ear, may be a PPG/SpO2 sensor 140, a temperature sensor 130 or a combination of the two; the second auxiliary unit, attached on the opposite side of the head, may be a second electrode 120 (the first electrode 110 being embedded in the casing of the unit and not visible behind the ear.

In one embodiment, shown in FIG. 5, two ear-wearable units are included in the system—one designed to be worn next to the right ear—and one designed to be worn next to the left ear. In such case, the two units (denoted primary unit 100 and secondary unit 100') may be substantially identical (or mirroring one another), but this is not necessarily so. The two units may also share functionalities between them, thereby utilizing the confined space of the casings efficiently. For example, main battery and out-going communication unit may be located in one of these units, while a smaller battery and more sensors may be located in the other unit.

FIG. 6 illustrates a perspective view of the client head with than area A indicated behind the ear. At area A, there is a depression between the skull and the lower jawbone. This area is ideal for sensing body temperature as well as taking PPG readings, as it is close to a major artery (the carotid, which runs from the heart to the head) as there is no bone, muscle or thick membrane in between the artery and the skin that blocks the Infra Red (IR) radiation that the artery emits. The location is therefore ideal as it provides exact temperature readings from the IR radiation. For the same reasons, a reflective pulse oximeter will get very good reflective results. Furthermore, the earlobe casts a shadow over the area which provides a dark cell in which PPG readings can be accurately taken, without ambient light interfering with the readings.

FIG. 7 illustrates a diagram of view of a client head with an exemplary embodiment of the ear device in position behind the right ear. FIG. 7A is a magnification of the sensors region of the ear device in position behind the ear, in between the lobe and the aforementioned depression (area A).

In the depicted embodiment of FIG. 7, the exemplary main unit is similar to the unit depicted in FIGS. 1A-B. The sensor abutting the skull is a thermometer operable to measure a body temperature of the client. In one embodiment, the thermometer is an IR sensor 130 that measures the IR radiation emitted from the carotid artery. In another embodiment, the thermometer is a thermistor such as the one depicted in FIG. 8, which is discussed below. In yet another embodiment, the thermometer may be integrated with the PPG sensor.

The ear device 100 further includes a reflective SpO2 sensor 140 on the side of the device abutting the back of the earlobe. As discussed elsewhere, the LED of the SpO2 sensor emits light at the lobe which is reflected back into the photodetector and analyzed to calculate the peripheral oxygen saturation level, amongst other vitals. It is made clear that the exemplary embodiment discussed heretofore, like all the exemplary embodiments, may be realized in other configurations, modifications, variations and combinations as would be obvious to one skilled in the art in view of the embodiments disclosed herein.

FIG. 8 illustrates a diagram of an exemplary embodiment of the thermometer of the immediate system. FIG. 8 depicts an exemplary thermistor 130' which can be used to substitute the IR thermometer 130 of FIG. 7 or as the thermometer in any of the preceding embodiments. Casing 132 houses the thermistor 134. The casing is filled with a pocket of air 136 which insulates the thermistor from the surrounding environment. The contact area 138 of the sensor is made of sheet metal, with the thermistor 134 abutting the inner surface of contact area 138. The thermistor is held in place by electrically and/or thermally conductive adhesive 139. The outer surface of the contact lies against the skin of the client, preferably in the depression behind the ear (area A) as depicted in FIG. 7. The contact absorbs the body temperature until the thermistor reaches a 'steady state'. In the steady state, the thermistor is the same temperature of the body.

Figure 9:
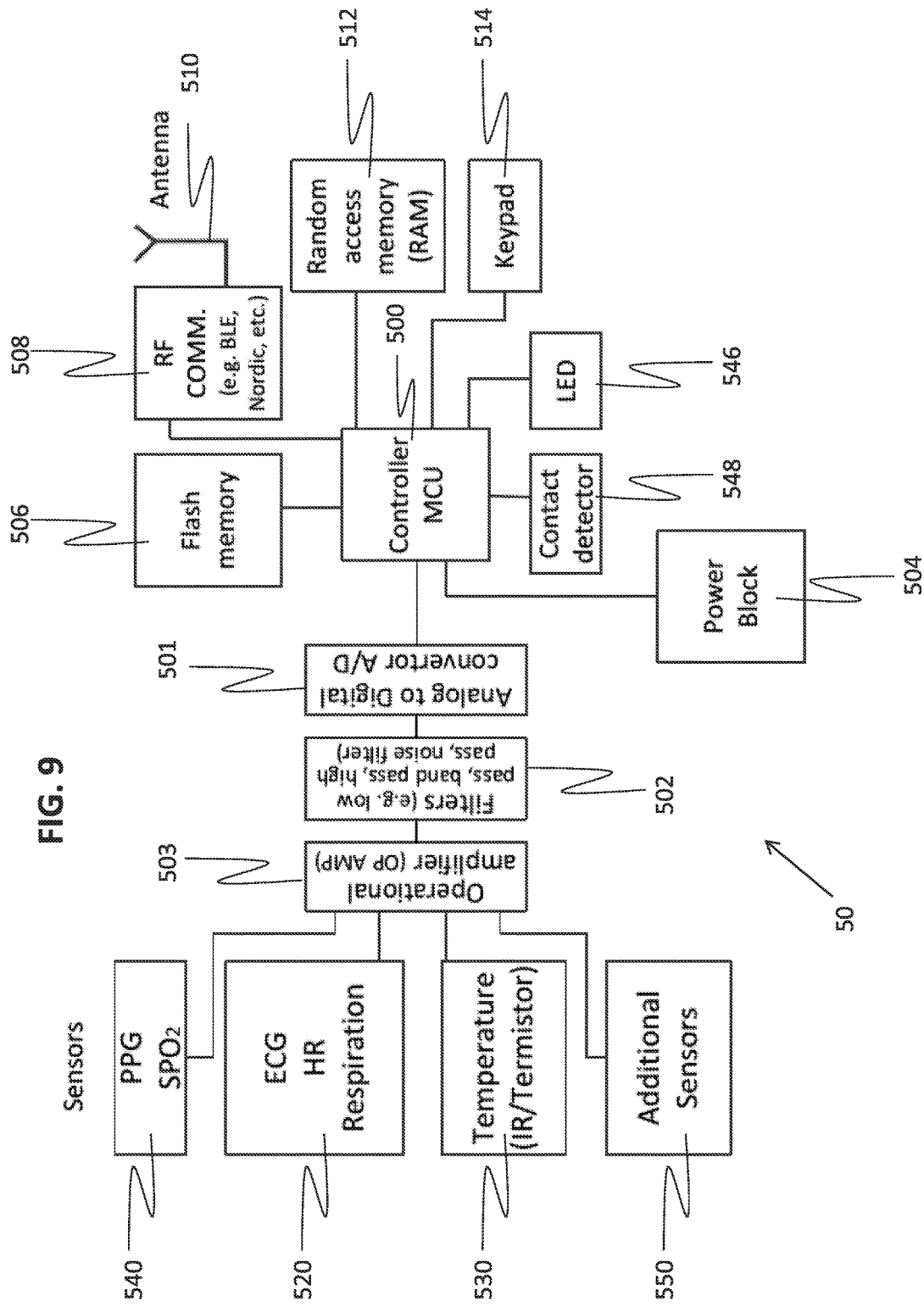
FIG. 9 is a functional block diagram illustrating an exemplary system.

FIG. 9 is a functional block diagram illustrating an exemplary system 50 for monitoring of vital signs, in accordance with the presently disclosed subject matter. It is noted that the presently disclosed system may include any variation of two or more of the various components illustrated in FIG. 9, as well as additional components. The functionality of each independent component illustrated in FIG. 9 is clear to any person of ordinary skill in the art, and is therefore not discussed in here in great detail.

The exemplary system 50, as depicted in FIG. 9, includes the following components: a microcontroller 500, an analog to digital converter 501, filters 502 (e.g. low pass, band pass, high pass, noise filter etc.), an operational amplifier 503, a power block 504 (such as a rechargeable battery, a replaceable battery etc.), a storage device 506 (e.g. flash memory), a wireless transceiver 508 which sends and receives radio frequency (RF) signals (e.g. BT, BLE, Nordic, ZigBEE, etc.) via an antenna 510, a Random Access Memory (RAM) 512, an input device such as a keyboard 514. The system further includes one or more sensors which are either integrated in a main unit or part of a remote auxiliary unit which may be connected to the system via a cable or wirelessly connected. Exemplary sensors include: a PPG/SpO2 540, an ECG/heart rate/respiration sensor 520, a temperature sensor (IR or thermistor) 530 as well as other additional sensors 550.

In any of such combinations of two or more components, the selected components may be included in a single casing designed to be worn behind one ear, in two such casings, or in one or more such casings as well as an additional unit (e.g., an auxiliary unit and/or a gateway as discussed below).

Figure 10:
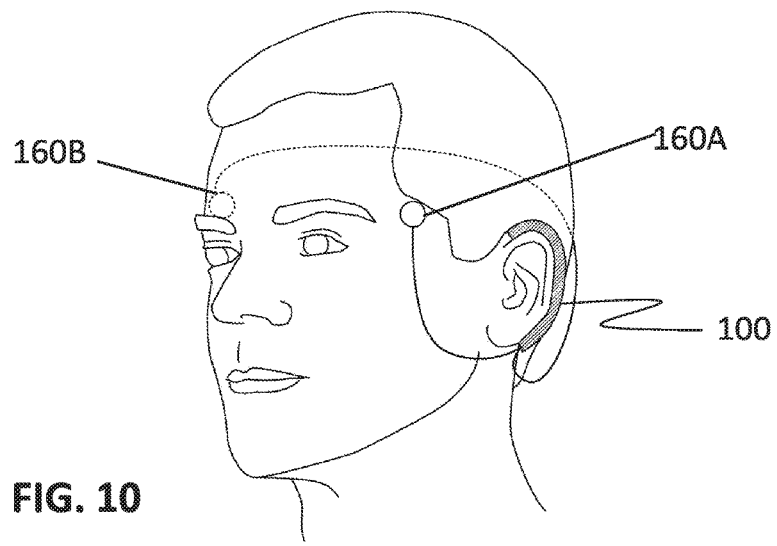
FIGS. 10 and 11 are diagrams of exemplary embodiments of the system on a client.

FIG. 10 illustrates a diagram of an exemplary embodiment of the system as implemented on a client. In the Figure, the ear piece includes two electrodes connected to the ear piece by cables. The ear piece has an internal power source and processor capable of deciphering the signals received from the sensors. From the various signals, the system can identify the Heart Rate Variability (HRV) of the client. HRV is the physiological phenomenon of variation in the time interval between heartbeats as measured by the variation in the beat-to-beat interval. By applying specialized algorithms, the HRV can be analyzed to determine the stress level of the client.

Once a stress issue has been identified, a decision can be made to provide electrical pulses to specified areas of the body, via special electrodes 160A and 160B. In the Figure, the electrodes are positioned by each of the temples and adhered to the skin with a patch. The electrodes may be placed in other effective locations such as the jaw, forehead, neck, shoulders, etc.

Exemplarily, the patch may comprise a biocompatible adhesive material on its underside, which may comprise an adhesive layer. The underside of the patch may comprise, for example, an aqueous polymer material or layer, such as a gel. The patch may comprise a hydrogel material. Any conventional gel or adhesive material capable of maintaining the patch against the client's skin for extended periods of time, such as one or more days may be used. Ideally the patch is capable of removal and reapplication once or a small number of times such that each patch could be used for up to, or greater than, one week.

The pulse regimen, as subscribed by the system or by a medical practitioner, is administered to the client via the electrodes. The frequency and amplitude of the pulses is controlled by the processor of the ear device according to instructions that may be provided wirelessly via the gateway, or predefined in the system programming. The pulses can be applied to alleviate muscle pain, headaches, toothache, infections and even lower stress and improve the client's mood. The pulses may be for the purpose of stimulation, calming, numbing pain and the like. The electrodes and sensors create a closed-circuit bio-feedback system.

Figure 11:
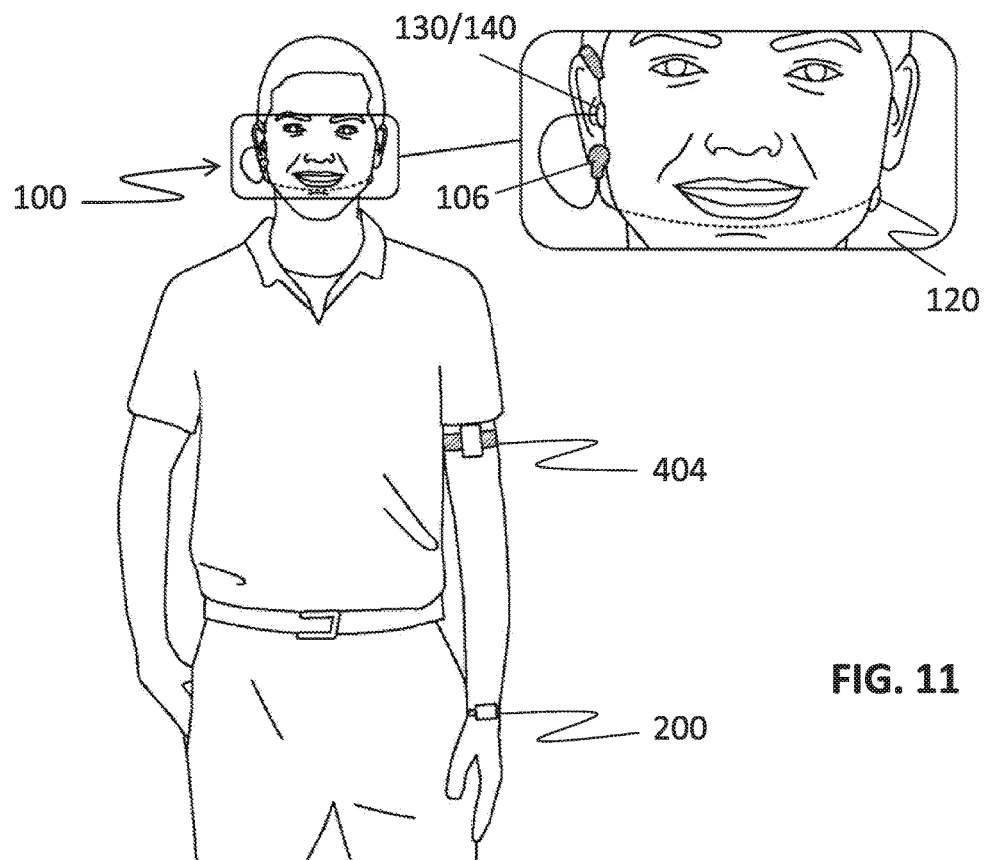

FIG. 11 is a diagram illustrating an example of the aforementioned system for monitoring of vital signs, in accordance with the presently disclosed subject matter, when worn by a person.

In addition to the various sensors, modules and components discussed above, the primary unit 100 may also include short-distance communication module (e.g. a radio frequency (RF) communication module) for communicating with a separate gateway unit 200. The gateway unit may be a dedicated unit which is part of the system, or another communication-enabled computer system such as a handheld/mobile device such as a smartphone, laptop, mini tablet or tablet may be carried in a pocket, dedicated carry case, purse or shoulder bag. In one embodiment, the gateway is also designed to be worn by a person (e.g. on the hand, on the waist), and includes connectors for connecting the gateway to the person (e.g. a belt, a wristband, etc.) or to an article worn or carried by the client (e.g. attached via a hook and look arrangement, a belt clip, etc.). The communication between the main unit and the gateway may be wireless (e.g. as illustrated) and/or wired communication.

The gateway unit includes a short-distance communication module for communicating with the primary unit (and possibly with other components—such as additional sensors located on the client), a processor, a memory and a long-distance communication module for communicating with an external backend computer (e.g. a server) distanced from the client by at least 3 meters, possibly hundreds or thousands of meters away, or even more. For example, the long-distance communication module may enable communicating with the backend computer ever the internet or over a cellular phone/data connection.

It is noted that gateway may further include additional components, such as additional sensors 400. Such sensors may include a blood pressure sensor 404, urine level sensors, urine sensors, medication level sensors, medication inducing sensors, etc. Such sensors or other sensors which are not included in the primary ear-wearable unit 100 may also be external to the gateway 200 and communicate detection results to the gateway using wireless and/or wired communication (see FIG. 12). Optionally, the gateway may include (or may directly communicate with) sensors of types which are not included in the casing of the primary unit.

Referring to the system in general (examples of which were discussed with respect to FIGS. 1 through 12), the system includes at least a main unit 100 which is operable to be worn on an ear (e.g. in any of the ways in which various hearing aids, earphones, earbuds and/or headsets connect to the ear or otherwise attached to it).

The casing of the main unit includes a processor (e.g. micro-controller unit MCU 500 of FIG. 9) which is configured and operable to receive detection results from one or more sensors of vital signs of a client. The one or more sensors may be located inside the casing of the main unit, and/or external to it, e.g. as discussed above. At least one of the sensors is either included in the aforementioned casing, or connected to it wirelessly.

The processor (which may be hardware and/or firmware processor) is configured and operable to control operation of the main unit (and possibly also of external components, e.g. external sensors), to collect the signals received from the one or more sensors, to process the signals to provide a medically significant result and/or a biologically significant result (e.g. which data should be transferred to a backend remote unit for further processing; that body parameters exceeded norm values, e.g. heartrate level indicate that a medication should be taken by the client, and so on and so forth).

In order to scale down the size of the primary unit and/or the gateway, lower costs, and reduce energy consumption, an exemplary processor is the nRF52832 System-on-Chip (SoC). The SoC is a powerful, highly flexible ultra-low power multiprotocol SoC ideally suited for Bluetooth® Smart ANT® and 2.4 GHz ultra low-power wireless applications. The nRF52832 SoC is built around a 32-bit ARM® Cortex™-M4F CPU with 512 kB+64 kB RAM. The embedded 2.4 GHz transceiver supports Bluetooth Smart, ANT and proprietary 2.4 GHz protocol stack. The nRF52832 SoC of produced by Nordic Semiconductor ASA, Oslo, Norway. The aforementioned SoC, or a similar component, has an integrated processor that is strong enough—and an internal memory that is big enough—to run the entire system (SpO2, temperature, memory, RF, LEDs etc.) and a storage memory that is big enough to store the algorithms that are run by the ear device on the SoC storage memory. As such, there is no need for an additional processor or added external memory.

The main unit further includes a close-range communication module (e.g. "RF COMM." 508 of FIG. 9) for communicating with a gateway unit, which is operable to receive from the processor of the main unit information that is based on the signals collected by the sensors—whether raw data or processed data. The gateway is further operable to transfer to the back-end unit information which is based on the information transmitted by the processor and possibly also from additional sensors, e.g. as discussed above. It is noted that the gateway may be operable to further process information provided by the processor of the main unit before sending information to the back-end system—processing which may have medical significance, communication significance, filtering or selection of specific information, etc.

It is noted that the main unit and/or the gateway may also receive information and/or instructions from the backend unit.

The gateway may be part of the system or external to it.

It is noted that information based on the information collected by the sensors may be transmitted to the backend unit (and/or to the gateway) in real time (or near-real-time), but this is not necessarily so, and such information may also be transmitted intermittently.

The system may further include a memory unit (either located in the main unit or elsewhere), such as storage device 506, of FIG. 9, for storing information collected by the sensors, either for routine operation and/or for when communication with the backend unit fails.

Although not common, it is well known in the art that different components of a system that are supposed to be wirelessly connected to each other are sometimes not able to connect. In the immediate system, when the remote sensors and/or the primary ear unit cannot connect with the gateway, some essential vital signs information cannot be broadcast to the backend unit. For example, if the system is implemented in a hospital setting, with ambulatory patients broadcasting vital signs information to the cloud and from there to the nurses' station. If a patient suddenly has a medical incident such as shortness of breath or atrial fibrillation it is imperative that the vital signs information is transmitted to the nurses' station immediately. If the sensors or ear device cannot contact the gateway, the information will not be passed along. In such a case, the system activates a backup operation where the sensors/ear device 'meshes' with sensors or other devices from a different patient.

Meshing allows the data to be transferred in a daisy chain between sensors of different patients. The ear device broadcasts to an ear device or gateway of a second patient. The data is identified as coming from the first patient and is sent via the cloud to the nurses' station. There, the data is presented as data from the first patient, even though the gateway of the second patient delivered the information. In an extreme case, where the gateway of the second patient is also not working, the ear device (or other sensor) sends the data to an ear device of the second patient and the ear device of the second patient sends the data to the ear device of a third patient. The third ear device sends the data to gateway and from there to the cloud. At each point along the 'daisy-chain' of devices, the data is identified as belonging to the first patient.

Figure 13:
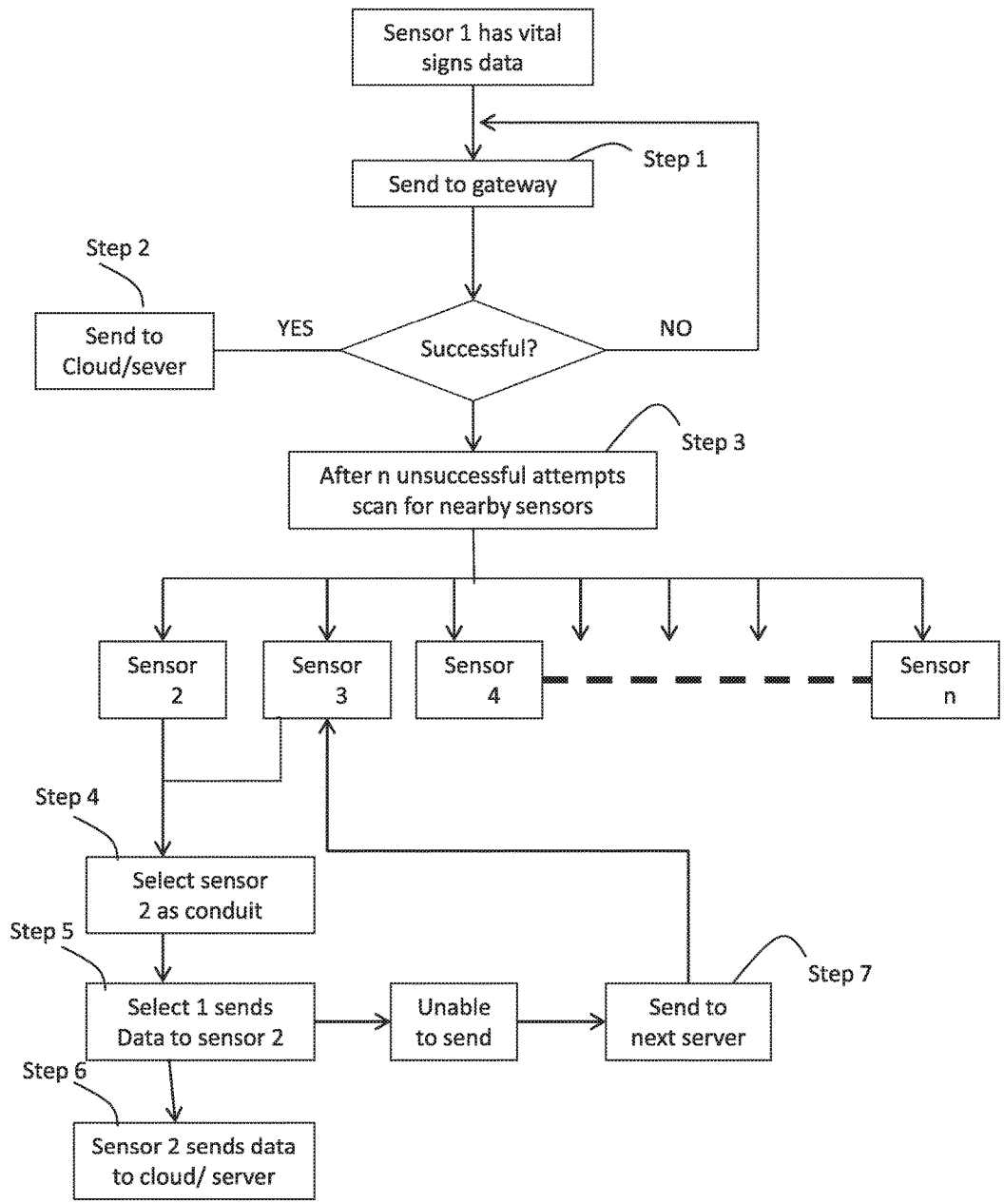
FIG. 13 is a flow diagram of the meshing procedure.

A clear procedure was followed in the aforementioned exemplary scenario. FIG. 13 illustrates a flow diagram of the meshing procedure. In step 1 a first sensor attempts to send data to the first gateway. If successful, the gateway transmits the data to the cloud in step 2. If the attempt fails then after a number of unsuccessful attempts the system understands that there is a communications problem and starts scanning for nearby sensors (i.e. from a different system of the same type, e.g. on a second patient) in step 3. In step 4, a second sensor is detected and selected and the first sensor asks the second sensor whether the second sensor will act as a conduit for the first sensor to send information to the cloud (or other remote destination). In step 5 the first sensor receives an approval to the request, the first sensor transmits the relevant data together with identifying data for the patient and for the sensor as well as a notification that there is a problem between the sensor and the gateway of the first patient. In step 6, the data is send successfully. If the second sensor cannot contact the second gateway, or the gateway cannot transmit the information to the cloud (or other destination), then, in step 7, the second sensor (or gateway) transmits the aforementioned data to a third sensor (or gateway) and so on as needed until the information gets to the desired destination.

Optionally, the main unit (and possibly other components of the system such as the gateway or auxiliary sensors) may be waterproof, enabling the client to shower or bath while the system is operating.

Optionally, the system may include protection mechanisms which are based on sensor data and dedicated software, so that when the client is in physical recovery and is performing physical activities as part of the recovery process, the system may guide the client (e.g. via the speaker) based on predetermined criteria (e.g. if the heartrate rises above or falls below a threshold).

It is noted that the system may further include one or more components which are designed to affect a body of the patient in response to an instruction provided by a processor of the system. For example, the system may include an electrical contact for applying voltage from the system to the body of the client, a vibrator for introducing vibrations to muscles, bones or other tissues of the client, and so on (see FIG. 10).

FIG. 12 is a diagram illustrating an example of the immediate system for monitoring of vital signs, in accordance with the presently disclosed subject matter. The system may include any one or more of the following sensors (integrated into the main unit or into the gateway or external to both):

A. A primary electrode 110 (see FIG. 1A/B) built into the main unit, made from a metallic plated material (e.g. biocompatible material) which is operable to be pressed against skin of the client, thereby creating an electric connection between the main unit and a body of the client.

B. A secondary electrode 120, built into the secondary unit 100' (in a similar fashion) and/or located at an end of a cable, operable to be connected in the vicinity of the other ear of the client (i.e. other than the ear next to which the main unit is to be placed). This enables to create the vector required for ECG measurements (e.g., see FIGS. 1A-B, 2A, 4, 10 and 12).

C. A PPG module/pulse oximeter 140 operable to monitor blood oxygen levels (and/or PPG) over prolonged periods of time (e.g. minutes, hours, days). Optionally, the measurement can be executed either by a sensor with a wire extending from the main unit (or the secondary unit) into an ear of the client (see for example FIG. 4), or by a sensor 140C clipping onto an earlobe of the client by an earlobe attachment 106, or by a sensor built into the main (and/or secondary) unit, directing towards the skull of the client (preferably pressed against the head), when the respective unit is worn by a client (see for example FIG. 7/7A). It is noted that the relevant area of the skull has no muscles or movement which would interfere, and a dark cell for PPG may be created for acquiring a clean PPG measurement.

D. A thermometer 130 (e.g. an IR thermometer 130 or a thermistor 130') operable to measure a body temperature of the client. Optionally, the thermometer may be integrated with the PPG sensor (e.g. both located on an end of the same cable which may be introduced into an ear of the client). The thermometer may be located in any one of the locations discussed with respect to the PPG sensor, and may also be located next to the depression located behind the respective ear of the client, where blood vessels extend which enable measuring of the temperature, see FIG. 7.

E. A connector or a permanently fixed cable, enable to perform EEG and/or stimulation of the nerves, e.g. in order to reduce or to diminish altogether headaches, tensions, stresses, anxiety, etc.

F. Auxiliary sensors which may include one or more of a PPG sensor 402 worn on a finger of the client, an upper-arm cuff-like sensor 404 which is adapted, among other things, to measure Blood Pressure and Heart Rate, and urine level sensors, urine sensors 406, medication level sensors, medication inducing sensors, etc.

In preferred embodiments, the system includes a chest patch 408 which is preferably adhered to the upper left side of the sternum. Exemplarily, the patch may comprise a biocompatible adhesive material on its underside, which may comprise an adhesive layer. The underside of the patch may comprise, for example, an aqueous polymer material or layer, such as a gel. The patch may comprise a hydrogel material. Any conventional gel or adhesive material capable of maintaining the patch against the client's skin for extended periods of time, such as one or more days may be used. Ideally the patch is capable of removal and reapplication once or a small number of times such that each patch could be used for up to, or greater than, one week. Such a patch is referred to hereafter as a 'disposable' patch.

The patch may include a wireless component capable of RF communications with the gateway and/or the primary ear piece and other sensors. In one embodiment, the patch is a disposable patch which includes basic sensors and wireless communications. In other embodiments, the patch is disposable with a connector 408a (or connectors) for attaching one or more sensors and a wireless communication module.

Additionally or alternatively, a small (reusable) hardware unit with minimal component can be attached to the connector. For example, the small hardware unit (not shown) can include some or all of: amplifiers, filters, analog-to-digital converters, memory and a simple processor with short range RF component. The unit acquires the electrical signals from the chest device (patch), filters and digitizes the signals and sends them to the ear unit for analysis. The ear device analyzes the received signal together with all the signals acquired by the ear device itself. The ear device therefore serves as the main processing unit that handles all the signals in the system. The memory is for cases where the hardware unit loses RF communications with the ear unit.

In yet another embodiment, the patch is disposable with a connector piece 408a adapted for the ECG sensor 120 (see FIG. 1A), or a similar sensor (e.g. coupled to the gateway) to clip onto the connector piece. The patch monitors heart functions and updates the system either periodically or when an irregular or unexpected heart function is sensed. In some embodiments, the chest patch includes a local microcontroller and memory configured to hold algorithmic data which processes the vital signs readings into meaningful medical data and transmits the processed results, or even sounds an alarm (or transmits an emergency notification) when the system determines that there is a medical emergency.

Figure 15:
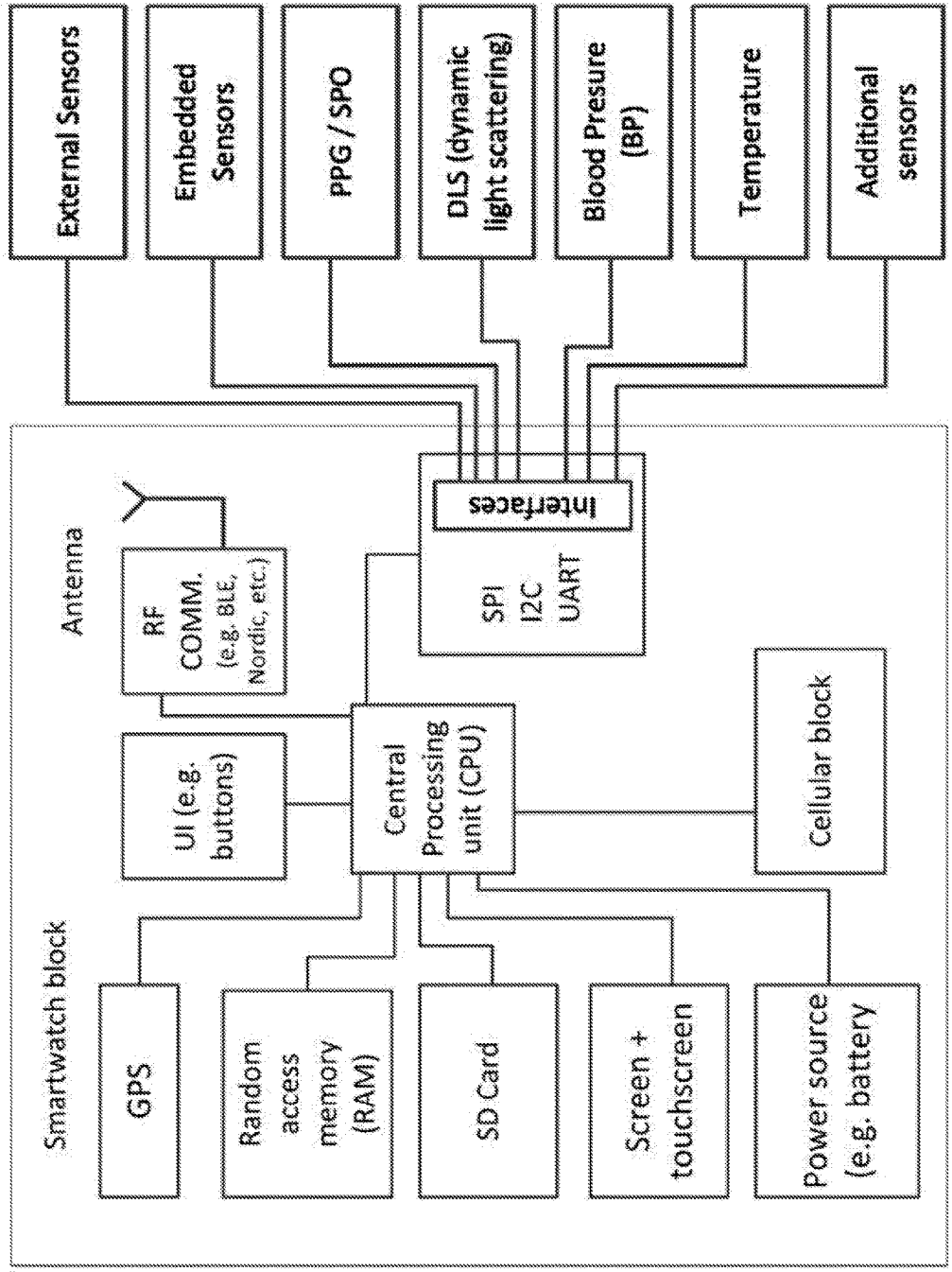
FIG. 15 is a block diagram of the gateway as exemplarily embodied in a Smartwatch.

Reverting to the gateway 200, it is noted that the gateway may be implemented as a cellular watch. FIG. 15 illustrates a high-level block diagram of the gateway 200 as exemplarily embodied in a Smartwatch. Gateway 200 which includes short range RF communication module, a touch screen, a data connection (e.g. USB interface, SPI, 12C, UART etc.) for connecting biological sensors, a CPU, RAM, storage (e.g. an SD card), a power source, a cellular block for cellular voice and/or data communications, a GPS and other components (e.g. a socket for connecting a charger).

The gateway 200 may communicate with the main unit 100 (or other components of the system (e.g. secondary unit 100', sensors 402, 404, 406 etc.) using the short range RF communication module using an RF communication protocol (e.g. Zigbee, BLE, 433/900 MHz, etc.). Optionally, the gateway may interface with biological sensors via a cable, or in a wireless manner. Exemplary biological sensors include: PPG/SpO2, BP, temperature as well as additional sensors. Some sensors may be external with others may be embedded in the gateway device. Exemplarily, a dynamic light scattering (DLS) may also be operationally coupled to the gateway device.

Optionally, settings and configurations of the system may be determined using a user interface (UI) of the gateway, and/or using an external computer communicating with the system (e.g. a smartphone, using a password protected application).

Optionally, settings and configurations of the system may be determined in response to instructions received from the backend unit 300, or from a dedicated software (e.g. application) running on a personal computer (PC), tablet computer, smartphone, etc.

The configuration of the system may be executed at a beginning of the service (for a specific client), and optionally also at other points in time, if required.

Optionally, the gateway 200 enables two-ways communication between one or more of the sensors 402-406 and the backend unit 300, so that if a medical personal (operating the backend) requires specific information, execution of another measurement, information from only some of the sensors, etc., such operator of the backend unit can send a message for the gateway, instructing the gateway to address the sensors for execution of such a command.

Optionally, the gateway may serve as a second handheld device communication of the client (e.g. in addition to his everyday cellular phone), so that if there is a need to communicate with the client (e.g. by the medical personnel operating the backend), communication may be initiated with the gateway, which can relay it through the short range RF communication to the headset (using a speaker and microphone), and the user can listen to the conversation from the speaker located next to her ear.

Optionally, the gateway may be operable to execute various algorithms to process the data provided to it by the sensors, to generate medically significant data, as discussed above.

Figure 12A:
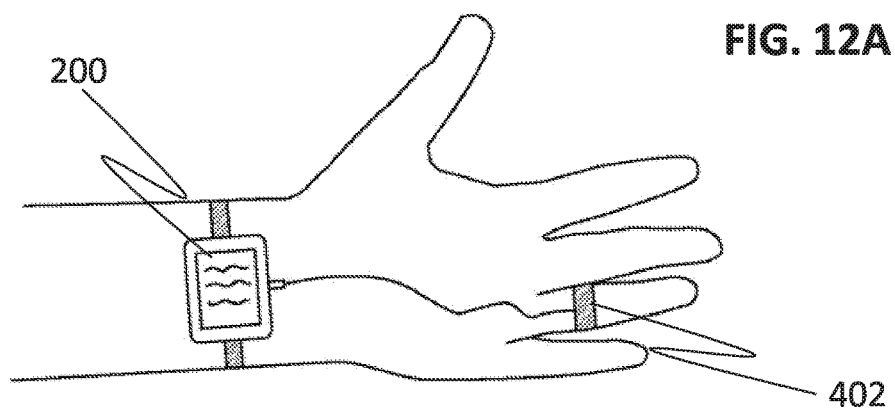
FIG. 12A, 14A/B are diagrams illustrating examples of the gateway as an integrated device.

Referring to the example of FIG. 12A, it is noted that optionally the gateway may include an interface enabling connection to the gateway of a data cable (e.g. USB cable) with a PPG sensor to the gateway, thereby enabling the PPG sensor 402 to be placed on a finger of the client. The PPG sensor may monitor a signal from the finger and provide it to the gateway, where it can be processed and displayed on a screen of the server, or sent to the backend (or another external system).

In addition to a PPG sensor, other sensors may also be connected through such a data interface (e.g. USB socket) of the gateway, for sampling other physiological signals, and passing them to processing in the gateway. Such sensors may be located on any part of the body of the client.

Figure 14A:
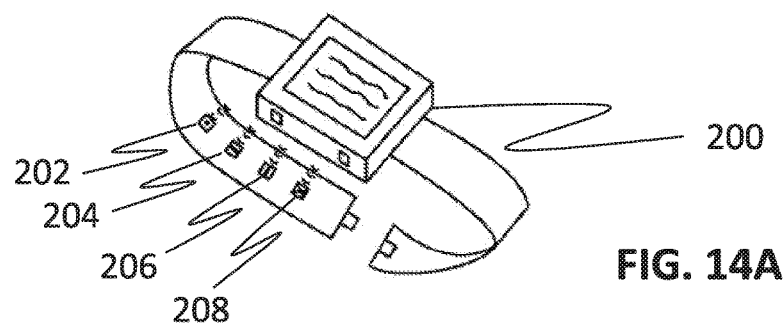
Figure 14B:
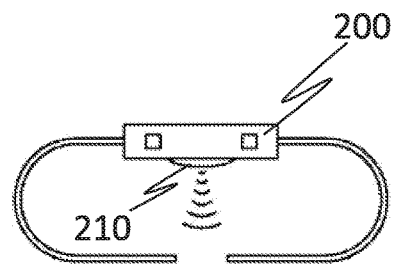

FIGS. 12A, 14A and 148 are diagrams illustrating examples of the gateway as an integrated device (integrating a cellular communication device and a medical device), in accordance with the presently disclosed subject matter.

Optionally, the gateway may be a combination of a cellular smart watch which includes an ordinary cellular platform (e.g. iOS or android based) or any other operating system, and medical modules 202, 204, 206, 208 and 210 which are placed against a wrist of the client when the latter wears the gateway on its arm (using a wristband, as illustrated) and which are operable to measure signals from the wrist area, and which provide data regarding a medical condition of the client (e.g. temperature, oxygen levels, and any of the sensor types discussed above).

A method for monitoring of vital signs is hereby disclosed—the method including:

a. Monitoring by one or more sensors vital signs of a client, wherein at least one of the sensors is located in a unit worn adjacent to an ear of the client (such sensors may measure, for example, any one of the data types mentioned above, such as BP, oxygen levels, temp., etc.);

b. Providing signals collected by the one or more sensors to a processor located in the unit;

c. Transmitting information based on the collected signals by the processor to an external unit, over a wireless connection.

Referring to the examples set forth with respect to the previous drawings, this method may be executed by the previously disclosed system, and any variation discussed with respect to that system may be implemented, mutatis mutandis, with respect to the method.

The stage of monitoring may be preceded by a stage of placing the unit on (or otherwise next to) an ear of the client. The stage of placing may be executed by the client herself, by a professional, etc.

The stage of transmitting may be followed by a stage of receiving from a backend unit instructions which were generated based on the data transmitted by the processor.

While certain features of the invention have been illustrated and described herein, many modifications, substitutions, changes, and equivalents will now occur to those of ordinary skill in the art, it is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention.

We claim:

1. A vital signs monitoring system, the system comprising:
   (a) an ear device including: a curved body adapted to a shape of an ear, an upper end, a lower end, two opposite facing sides, a first side adapted to be proximal a skull and a second side adapted to be proximal an earlobe, said ear device comprising: (i) a temperature sensor adapted to sense a body temperature from a depression between a lower jawbone and skull;
   (b) a control system, comprising a processor and a memory, configured and operable to control operation of said ear device, to collect signals received from at least one sensor including said temperature sensor, to process said signals to provide medically significant results; and
   (c) at least one electrode operationally coupled to said ear device, said at least one electrode configured to deliver electrical pulses from a power source in said ear device to a skin patch operationally coupled to said at least one electrode.

2. The system of claim 1, wherein said temperature sensor is an infra red (IR) sensor configured to measure IR radiation at said depression, said IR radiation emitted from a carotid artery.

3. The system of claim 1, wherein said temperature sensor includes a thermistor.

4. The system of claim 3, wherein said thermistor is encased in a casing, insulated, and held in place by a thermally conductive adhesive, said casing having a thermally conductive surface adapted to abut said depression.

5. The system of claim 1, wherein said ear device further comprises:
   (ii) a first electrode built into an inner curve of said curved body, said first electrode configured to sense signal from behind said ear; and
   (iii) a second electrode distanced from, and in electric communication with, said ear device, wherein said first and said second electrodes are adapted to be positioned so as to create a vector required for acquiring electrocardiographic measurements;

wherein the first electrode and the second electrode differ from the at least one electrode operationally coupled to said ear device.

6. The system of claim 5, wherein said second electrode is operationally coupled to said ear device via one of: a cable and a wireless communications component.

7. The system of claim 1, wherein said ear device further comprises:
(ii) a blood oxygen sensor configured to receive signals that are processed to receive said medically significant results selected from the group including: a photoplethysmogram (PPG), a peripheral oxygen saturation (SpO2) measurement, a heart rate, a combination of at least two said results.

8. The system of claim 7, wherein said blood oxygen sensor is selected from the group including: a transmissive sensor and a reflective sensor.

9. The system of claim 8, wherein said blood oxygen sensor is embedded in said ear device.

10. The system of claim 8, wherein said blood oxygen sensor is operationally coupled to said ear device via a connection selected from the group including: a wired connection and a wireless connection.

11. The system of claim 8, wherein said ear device further includes an earlobe attachment that is adapted to abut an outer surface of an earlobe of said ear, said earlobe attachment including a photodector to receive light energy from a light source of said blood oxygen sensor during a transmissive pulse oximetry event.

12. The system of claim 1, further comprising:
(c) at least one additional sensor adapted to be in electrical communication with a body part so as to receive electrical signals from said body part, wherein said at least one additional sensor is in electrical communication with said ear device, said electrical communication effected by at least one of a wireless connection and a wired connection.

13. The system of claim 12, wherein said at least one additional sensor is an auxiliary ear device, wherein said auxiliary ear device has a curved body adapted to a shape of an ear and adapted to be worn a second ear on a facing side of a head, distanced from said ear device.

14. The system of claim 12, wherein said at least one additional sensor is selected from the group including: blood oxygen sensor, a heart rate sensor, a blood pressure sensor, a urine sensor, a urine level sensor, a medication level sensor, a medication inducing sensor and a combination sensor including at least two of said sensors.

15. The system of claim 1, further comprising:
(c) a gateway device including: a short-distance communication module for communicating with said ear device, a processor, memory, and a long-distance communication module for communicating with an external backend computer.

16. The system of claim 15, wherein said gateway device is embodied in a device selected from the group including: a handheld device, a portable computing device and a body worn device.

17. The system of claim 15, further comprising:
(d) at least one additional sensor adapted to be in electrical communication with a body part so as to receive electrical signals from said body part, wherein said at least one additional sensor in electrical communication with one of said ear device and said gateway device, said electrical communication effected by at least one of a wireless connection and a wired connection.

18. The system of claim 1, wherein said ear device further includes: an anchor member operationally coupled to said upper end of said ear device and adapted to support said ear device on said ear, said anchor member having a speaker embedded therein and a microphone embedded in said lower end of said ear device.

19. The system of claim 18, wherein said microphone is a wire microphone that extends out of said lower end of said ear device by manually manipulating a slider along a channel, said slider and channel integrated in said ear device.

20. A vital signs monitoring system, the system comprising:
(a) an primary ear device including: a curved body adapted to a shape of an ear, an upper end, a lower end, two opposite facing sides, a first side adapted to be proximal a skull and a second side adapted to be proximal an earlobe, said ear device comprising at least one sensor;
(b) a secondary ear device adapted to be worn a second ear on a facing side of a head, distanced from said primary ear device, said secondary ear device in electrical communication with said primary ear device, said electrical communication effected by at least one of a wireless connection and a wired connection;
(c) a control system embedded in said primary device comprising a processor and a memory, configured and operable to control operation of said primary and secondary ear devices, to collect signals received from at least one sensor, to process said signals to provide medically significant results; and
(d) at least one electrode operationally coupled to said primary ear device, said at least one electrode configured to deliver electrical pulses from a power source in said primary ear device to a skin patch operationally coupled to said at least one electrode.

21. A vital signs monitoring system, the system comprising:
(a) an ear device including: a curved body adapted to a shape of an ear, an upper end, a lower end, two opposite facing sides, a first side adapted to be proximal a skull and a second side adapted to be proximal an earlobe, said ear device including at least one vital signs sensor; and
(b) at least one electrode operationally coupled to said ear device, said at least one electrode configured to deliver electrical pulses from a power source in said ear device to a skin patch operationally coupled to said at least one electrode; and
(c) a control system, comprising a processor and a memory, configured and operable to control operation of said ear device, to collect signals received from said at least one vital signs sensor, to process said signals to provide medically significant results and to control delivery of said electrical pulses.

22. A vital signs monitoring system, the system comprising:
(a) an ear device including: a curved body adapted to a shape of an ear, an upper end, a lower end, two opposite facing sides, a first side adapted to be proximal a skull and a second side adapted to be proximal an earlobe, said ear device including at least one vital signs sensor; and
(b) a control system, comprising a processor and a memory, configured and operable to control operation of said ear device, to collect signals received from said at least one vital signs sensor, to process said signals to provide medically significant results;

and at least one electrode operationally coupled to said ear device, said at least one electrode configured to deliver electrical pulses from a power source in said ear device to a skin patch operationally coupled to said at least one electrode.

23. The system of claim 22, further comprising:
(c) a chest device operationally coupled to a biocompatible adhesive patch adapted to be adhered to skin, said chest device including at least some of: amplifiers, filters, analog-to-digital converters, a local memory and a local processor with a short range wireless communications component, wherein said chest device is configured to acquire electrical signals via said biocompatible adhesive patch, filter and digitize said signals and send said digitized signals to said ear device to process said signals to provide said medically significant results.

* * * * *